United States Patent
Miyakozawa et al.

(10) Patent No.: US 8,479,586 B2
(45) Date of Patent: Jul. 9, 2013

(54) DEVICE FOR FATIGUE TESTING A SPECIMEN

(75) Inventors: Tomokazu Miyakozawa, Derby (GB); Mark L. Brace, Trowbridge (GB); Caetano Peng, Derby (GB); Stephen R. Turner, Derby (GB); Ciaran A. Williams, Derby (GB)

(73) Assignee: Rolls-Royce PLC, London (GB)

( * ) Notice: Subject to any disclaimer, the term of this patent is extended or adjusted under 35 U.S.C. 154(b) by 0 days.

(21) Appl. No.: 13/399,272

(22) Filed: Feb. 17, 2012

(65) Prior Publication Data

US 2012/0240687 A1    Sep. 27, 2012

(30) Foreign Application Priority Data

Mar. 23, 2011   (GB) .................................. 1104864.2

(51) Int. Cl.
- G01B 7/16 (2006.01)
- G01L 1/00 (2006.01)
- G01N 3/08 (2006.01)
- G01N 3/00 (2006.01)
- G01N 3/02 (2006.01)

(52) U.S. Cl.
USPC ............... 73/778; 73/856; 73/831; 73/808; 73/806

(58) Field of Classification Search
USPC ............... 73/779, 826, 808, 788, 778, 831, 73/856
See application file for complete search history.

(56) References Cited

U.S. PATENT DOCUMENTS

| | | | | |
|---|---|---|---|---|
| 3,442,120 A * | 5/1969 | Anderson et al. | ............... | 73/805 |
| 4,643,035 A | 2/1987 | Murphy | | |
| 5,952,581 A * | 9/1999 | Lammers et al. | ............... | 73/831 |
| 6,023,980 A * | 2/2000 | Owen et al. | ..................... | 73/797 |
| 6,601,456 B1 * | 8/2003 | Davidson et al. | ............... | 73/808 |
| 6,732,591 B2 * | 5/2004 | Miles et al. | ................... | 73/808 |
| 6,813,960 B1 * | 11/2004 | Owen et al. | ..................... | 73/808 |
| 7,204,152 B2 * | 4/2007 | Woodward et al. | ............. | 73/794 |
| 7,204,153 B2 * | 4/2007 | Phipps | ............................ | 73/808 |
| 2002/0017144 A1 * | 2/2002 | Miles et al. | ................... | 73/808 |
| 2008/0092665 A1 * | 4/2008 | Melz et al. | ..................... | 73/841 |
| 2008/0223145 A1 | 9/2008 | Merendino | | |

FOREIGN PATENT DOCUMENTS

| | | |
|---|---|---|
| EP | 1 602 914 A2 | 12/2005 |
| FR | 2 680 003 A1 | 2/1993 |
| GB | 2 060 179 A | 4/1981 |

OTHER PUBLICATIONS

May 27, 2011 Search Report issued in British Application No. GB1104864.2.
Apr. 16, 2012 European Search Report issued in European Patent Application No. EP 12 15 5946.

* cited by examiner

*Primary Examiner* — Lisa Caputo
*Assistant Examiner* — Jonathan Dunlap
(74) *Attorney, Agent, or Firm* — Oliff & Berridge, PLC

(57) ABSTRACT

Apparatus for fatigue or mechanical friction damping measurement testing a specimen the apparatus including a body having opposing arms defining between them a space for receiving the specimen, one of the opposing arms having a fixture for securing the specimen, another of the opposing arms having a further fixture for securing the specimen, the fixture and the further fixture being adjustable to increase or decrease the relative distance therebetween, wherein the body includes an assigned vibration location to which excitation signals are applied during testing.

17 Claims, 4 Drawing Sheets

DEVICE FOR FATIGUE TESTING A SPECIMEN

The present invention relates to a device for testing a specimen and particularly for testing the high cycle fatigue (HCF) of the specimen. Of particular interest is the measurement of mechanical friction damping generated at locations which secure the specimen in location with another component.

Gas turbine engine fan aerofoils, compressor blades and stators and turbine blades and stators (collectively known as blades in this application) are subjected to a combination of low cycle fatigue (LCF) and high cycle fatigue stresses in operation of the gas turbine engine. These low cycle fatigue and high cycle fatigue stresses have a detrimental effect on the integrity of the fan blades, compressor blades and turbine blades. Particularly with stators, also known as vanes, the vibrations are significantly affected by mechanical friction damping through friction type contact joints at upper and lower feet.

The high cycle fatigue is a result of aerodynamic and other vibration excitation of the blades and the fundamental mode frequencies may vary from about 50 Hz for a fan blade up to several tens of kHz for some compressor or turbine blades. The maximum mode frequency is usually around 30 kHz. Further vibration modes are perceived in stators when both ends are restrained and these are commonly known as "bow mode".

High cycle fatigue damage quickly builds up due to the relatively large number of cycles in relatively short periods of time. The damaging effect of the mechanical cycles is exacerbated by the thermal cycles to which the gas turbine engine is subjected in operation. In order to design blades which are resistant to fatigue a good understanding of the alternating stresses a blade may tolerate for any vibration mode that may be excited in operation is required. The alternating stresses or vibration characteristic is significantly affected by contact conditions of vanes.

One apparatus that has been provided to measure both low cycle and high cycle fatigue is described in U.S. Pat. No. 6,732,591. This document describes equipment which can secure either end of a component to the tested through clamping means. The equipment has an actuator which moves the first and second clamping means relative to each other to provide either a tension load or a compression load. A shaker is acoustically coupled to one of the first and second clamping means to provide high cycle loads.

Such an arrangement is relatively complex and requires a large frame to surround it. The shaker load can only be applied in a few locations. The invention is intended to provide improved apparatus for testing particularly the mechanical friction damping and high cycle fatigue.

According to the invention there is provided apparatus for fatigue testing or friction damping measurement testing a specimen the apparatus comprising a body having opposing arms defining between them a space for receiving the specimen, one of the opposing arms having a fixture for securing the specimen, another of the opposing arms having a further fixture for securing the specimen, the fixture and the further fixture being adjustable to increase or decrease the relative distance therebetween, wherein the body comprises an assigned vibration location to which excitation signals are applied during testing.

One reason for adjusting the relative distance between the fixture and further fixture is to apply different levels of loading at the contact joints.

Preferably the body is a single piece which may be "C" shaped for holding a vane with the least extra friction loss with each of the opposing arms in fixed relationship to each other. Alternatively, the body may be "C" shaped and arranged such that a connecting portion connecting the opposing arms can have a length which may be varied.

The fixture may comprise a slot for receiving a portion of the specimen. Preferably the fixture may be provided within one of the opposing arms. As an alternative the fixture may be mounted to the opposing arm in replaceable loading block. The fixture may comprise other alternatives for securing the specimen such as a shaped post around which the specimen is secured or an aperture into which a protrusion on the specimen in inserted.

The further fixture may comprise a slot for receiving a portion of the specimen. Preferably the fixture may be provided within one of the opposing arms. As an alternative the fixture may be mounted to the opposing arm in replaceable loading block. The fixture may comprise other alternatives for securing the specimen such as a shaped post around which the specimen is secured or an aperture into which a protrusion on the specimen in inserted, Either the fixture or the further fixture may be mounted to its respective opposing arm by an actuator which is adjustable to move the further fixture relative to its respective opposing arm. The actuator may comprises a bolt having a thread which extends through the respective opposing arm and engages a complementary thread in a loading block, the loading block may provide the recess, slot or protrusion for securing the specimen thereto.

The assigned vibration location may be located on one of the opposing arms or on a connecting portion which extends between the opposing arms. The assigned vibration location may comprise a hole having a screw thread for receiving an exciter. The body may be provided with a plurality of vibration locations which may be selectively used to alter the high frequency experienced by the specimen.

Preferably the apparatus may further comprise an exciter engaged with the vibration location. The exciter may comprise a tuned mass and at least one piezoelectric element to vibrate the tuned mass. The exciter may also have a bolt which is secured to the vibration location. The piezoelectric elements may be annular discs and arranged such that the bolt passes through the centres thereof. The tuned mass may be removable from the piezoelectric elements and replaced with an alternative tuned mass.

Preferably the specimen is a vane for a gas turbine. Preferably the vane is manufactured to satisfy engine part requirements. The slots in the fixture and further fixture may be adapted to secure the vane feet and have a shape which corresponds to the mounting features within the gas turbine. The specimen may be a blade for a gas turbine. The fixture and further fixture may be adapted to secure the blade root with the blade extending away from the body in a direction which is perpendicular to the direction in which the connecting portion extends and perpendicular or parallel to the direction in which the opposing arms extend.

The invention will now be described by way of example only with reference to the accompanying drawings, in which.

Figure 1A:
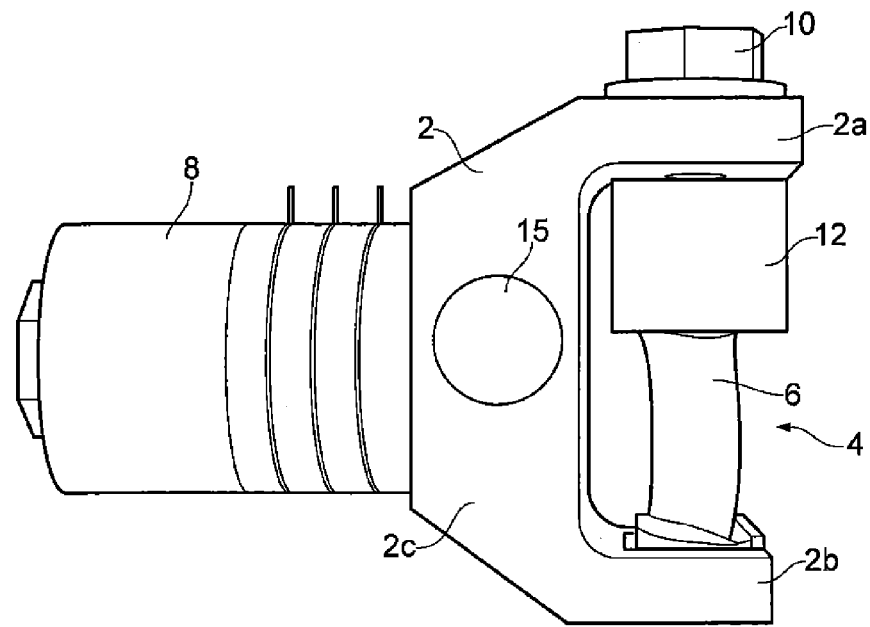
FIG. 1 depicts a side view of a stator clamping device with a piezoelectric exciter.

In FIG. 1a there is shown a stator clamping device used in High Cycle Fatigue testing or mechanical friction damping measurement. The device comprises a body 2 which has arms 2a, 2b that extend from a central connecting portion 2c, The arms define a space 4 which receives the test specimen 6. An exciter 8 is mounted to the body to provide high frequency excitation signals to the specimen. The body has a stiffness that is selected to maintain the arm spacing in use at a fixed distance despite the tension applied to the specimen by an actuator 10. The stiffness also permits the excitation signals to be accurately transmitted through to the specimen at the chosen frequency without attenuation or frequency shift.

A loading block 12 is provided within the space 4 to which one end of the specimen is attached. The loading block is secured to the actuator 10 by a screw thread such that rotation of the actuator causes relative movement of the loading block towards or away from the opposing arm 2b. The actuator in its simplest form as shown here is a bolt extending though an aperture provided in the upper arm 2a.

Figure 1B:
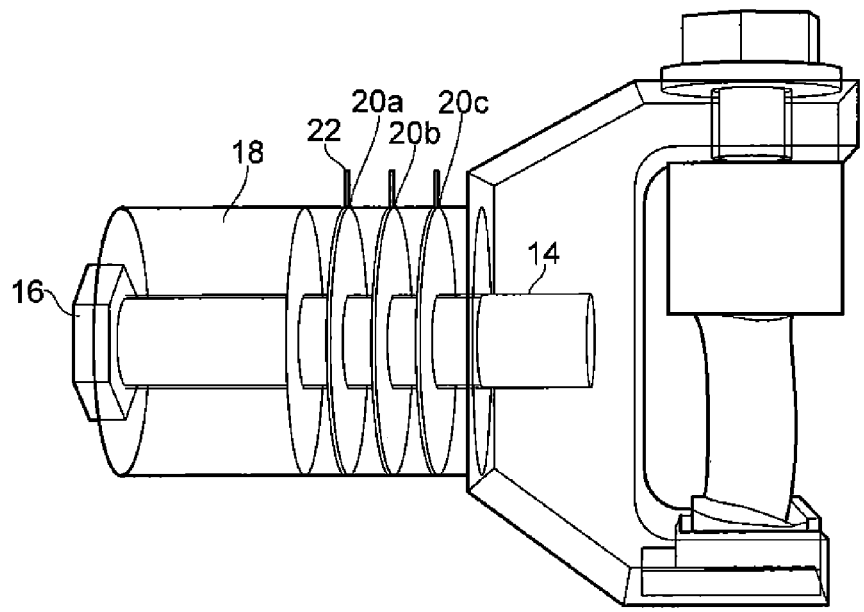

The exciter is mounted to the body at a vibration location 14 by a bolt 16 that extends through the exciter and into the body as shown in FIG. 1b. The bolt ensures good contact between the exciter and the body which permits the excitation signals to be accurately transmitted through to the specimen at the chosen frequency without attenuation or frequency shift.

The exciter comprises a tuned mass 18 and a piezoelectric body formed by a plurality of piezoelectric laminates 20a . . . 20b connected to an electrical source by wires 22. The tuned mass is replaceable with alternative tuned masses in order to change the vibration frequency of the exciter and similarly a number of other vibration locations may be provided on the body which permits the location at which the exciter is mounted to the body to be varied in accordance with the desired vibration mode to be investigated in the specimen.

The piezoelectric pack may be located to a side of the body which may excite torsion vibration modes on the excite torsion vibration modes. A vibration location 15 is marked on FIGS. 1a and 2a.

Figure 2A:
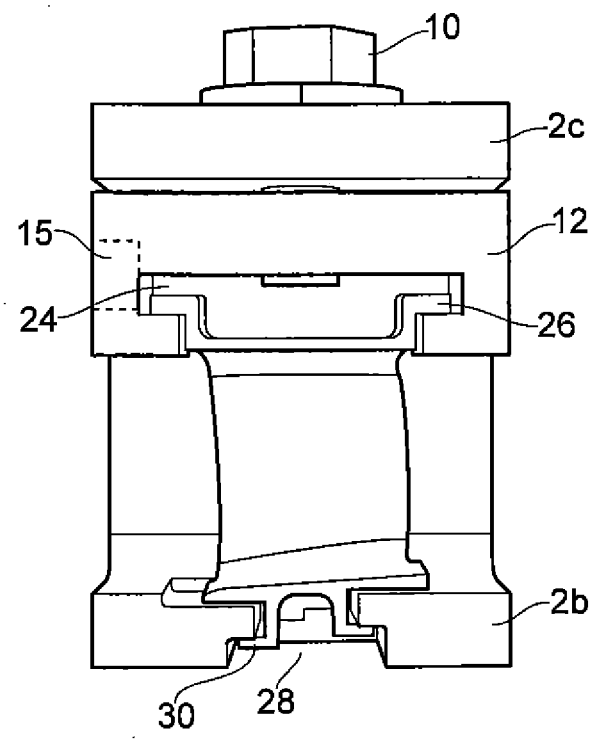
FIG. 2 depicts a front view of the stator clamping device of FIG. 1.
Figure 2B:
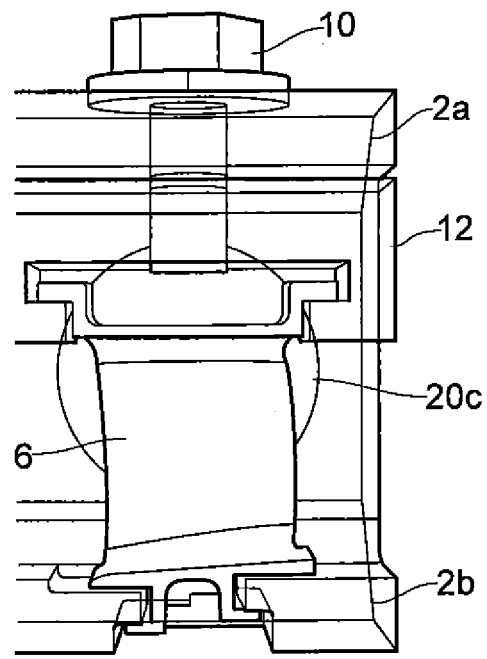

FIG. 2a and FIG. 2b depict a front view of the stator clamping block. The loading block 12 has a recess 24 which is adapted to receive the feet 26 of the specimen 6 and similarly the opposing arm 2a has a further recess 28 to receive a further set of feet on the specimen. Beneficially the arrangement represents the vane constraining conditions in a real engine by providing the friction type contact joints of a form used in a real engine.

Different levels of radial force can be applied by adjusting the actuator 10 to vary the distance between the loading block 12 and the opposing arm 2b to control the contact loads or conditions at stator feet. A load washer placed between the loading block and the arm to monitor the pulling or pushing force applied by the loading bolt.

The arrangement uses a low number of contact surfaces to reduce the friction losses.

The arrangement may also be used to detect one or more mode shapes of a secured specimen. The specimen is located in the loading block and a large contact load of over 1000N used to minimise or remove friction effects at the joint of the specimen with the loading block. The excitation frequency from the exciter cycled from a few thousand Hertz, possibly 1 to 2 thousand, through to several thousand Hertz, possibly 12 to 15 thousand or more.

The response of the specimen is monitored and optionally recorded through the cycle. As the cycle passes through a modal frequency the response increases from negligible displacement of the specimen up to a displacement in excess of 0.1 mm. The modal frequency and the response can be compared with values determined by modelling to validate the models. The detected frequencies and or mode shapes can also be compared with values taken at an earlier stage in the life of the specimen or with values taken from other specimens to determine whether the modes are changing and are those expected from the sample.

Figure 3:
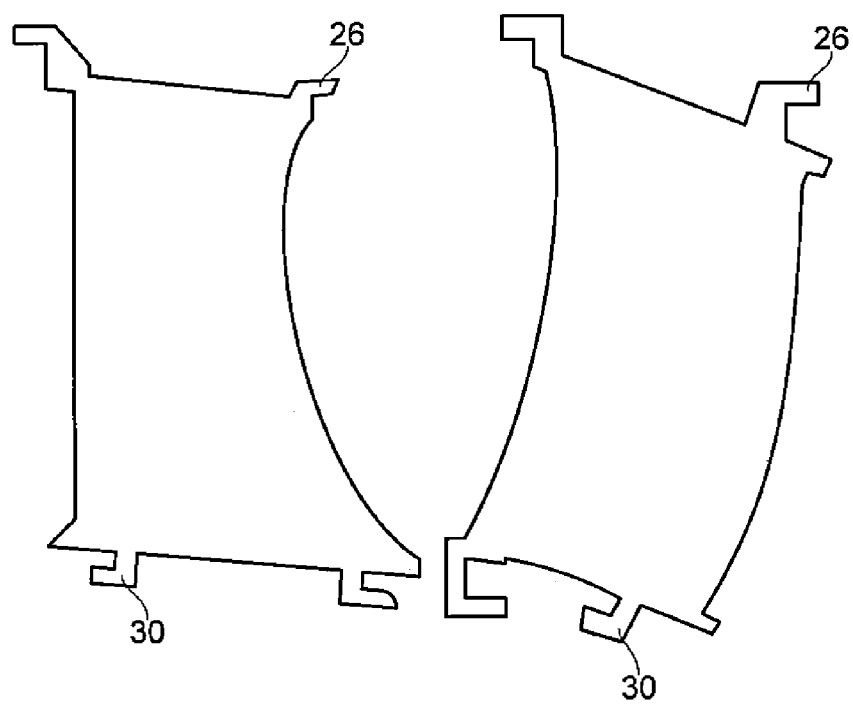
FIG. 3 depicts alternative arrangements for stator feet.

FIG. 3 shows two exemplary vanes which may be used as specimens in the test apparatus. As may be seen each vane has a different arrangement of feet with the feet being arranged to engage with different receptacles in the gas turbine. Where the testing apparatus is intended to hold stator vanes it will be appreciated that the upper and lower clamping features may be modified to hold many different types of stator vane end designs. If the vanes do not have appropriately arranged feet the vanes (or other specimens) may be secured using vane spindles or another arrangement. Where the apparatus is intended to apply compression to the specimen whilst applying excitation a further fixture design may be required. Such an arrangement could be readily determined by the person of skill in the art through appropriate testing.

Figure 4:
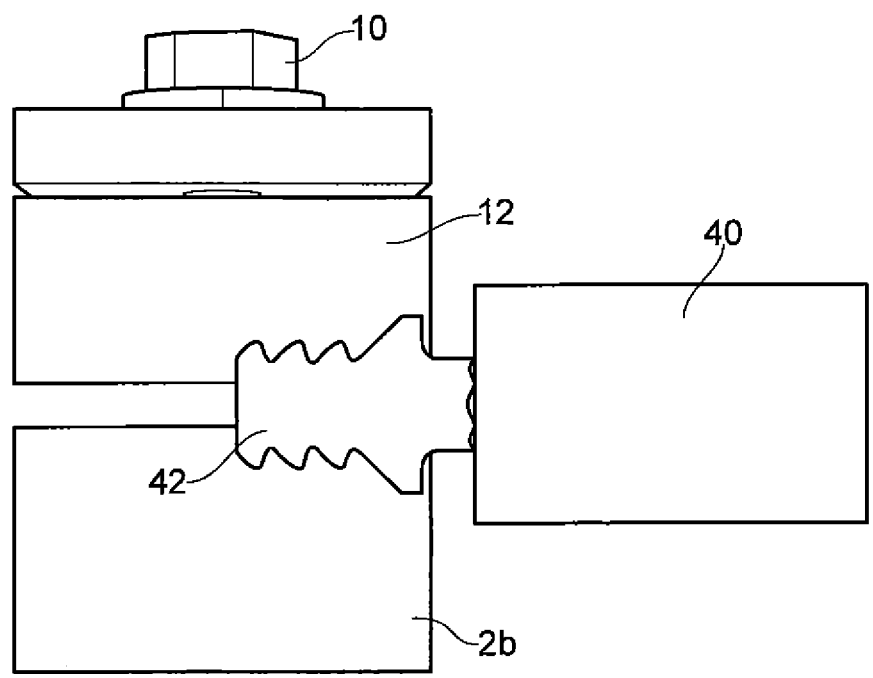
FIG. 4 depicts a view of a blade clamping device.

The apparatus can be used to test high cycle fatigue of cantilevered blades using apparatus described with reference to FIG. 4. In this embodiment the actuator 10 is used to move loading block 12 towards arm 2b. The arm 2b and the loading block are each provided with a shaped recess which engages the root—in this case a fir tree—of the cantilevered blade 40. Alternatively, the loading block may be split into two halves with the recess provided therebetween.

It will be appreciated that the apparatus as described herein offers significant advantages in simplicity of design, ease of use, and an ability to vary the modal excitation experienced by the specimen.

The actuator 10 may be any appropriate type of actuator e.g. hydraulic, pneumatic, or linear variable differential transformer.

The invention claimed is:

1. An apparatus for fatigue or friction damping measurement testing of a specimen, the apparatus comprising:
a body having:
opposing arms defining between them a space for receiving the specimen, one of the opposing arms having a fixture for securing the specimen, another of the opposing arms having a further fixture for securing the specimen, the fixture and the further fixture being adjustable to increase or decrease the relative distance therebetween, and
an assigned vibration location to which excitation signals are applied during testing,
wherein the body is a single piece.

2. The apparatus according to claim 1, the fixture having a slot for receiving a portion of the specimen.

3. The apparatus according to claim 1, the further fixture having a slot for receiving a portion of the specimen.

4. The apparatus according to claim 3, wherein the further fixture is mounted to its respective opposing arm by an actuator which is adjustable to move the further fixture relative to its respective opposing arm.

5. The apparatus according to claim 4, wherein the actuator comprises a bolt having a thread which extends through the respective opposing arm and engages a complementary thread in a loading block, the loading block providing the further fixture.

6. An apparatus for fatigue or friction damping measurement testing of a specimen, the apparatus comprising:
a body having:
opposing arms defining between them a space for receiving the specimen, one of the opposing arms having a fixture for securing the specimen, another of the opposing arms having a further fixture for securing the specimen, the fixture and the further fixture being adjustable to increase or decrease the relative distance therebetween, and an assigned vibration location to which excitation signals are applied during testing, wherein the assigned vibration location includes a hole having a screw thread for receiving an exciter.

7. The apparatus according to claim 6, comprising a plurality of vibration locations.

8. The apparatus according to claim 6, wherein the assigned vibration location is between the opposing arms.

9. The apparatus according to claim 6, further comprising an exciter engaged with the vibration location.

10. The apparatus according to claim 9, wherein the exciter comprises a tuned mass and at least one piezoelectric element to vibrate the tuned mass.

11. A method of testing a specimen in an apparatus as claimed in claim 6, the method comprising:

securing a specimen to the apparatus, and applying excitation signals to the assigned vibration location.

12. The method of testing according to claim 11, wherein a plurality of excitation signals are applied sequentially, at a plurality of different frequencies.

13. The method according to claim 11, further comprising the step of detecting the modal frequencies of the specimen.

14. The method according to claim 11, further comprising the step of recording the displacement of the specimen induced by the application of the excitation signals.

15. An apparatus for fatigue or friction damping measurement testing of a specimen, the apparatus comprising:

a body having:

opposing arms defining between them a space for receiving the specimen, one of the opposing arms having a fixture for securing the specimen, another of the opposing arms having a further fixture for securing the specimen, the fixture and the further fixture being adjustable to increase or decrease the relative distance therebetween, and an assigned vibration location to which excitation signals are applied during testing: and an actuator, the further fixture being mounted to its respective opposing arm by the actuator which is adjustable to move the further fixture relative to its respective opposing arm, the actuator including a bolt having a thread which extends through the respective opposing arm and engages a complementary thread in a loading block, the loading block providing the further fixture.

16. The apparatus according to claim 15, wherein the assigned vibration location comprises a hole having a screw thread for receiving an exciter.

17. An apparatus for fatigue or friction damping measurement testing of a specimen, the apparatus comprising:

a body having:

opposing arms defining between them a space for receiving the specimen, one of the opposing arms having a fixture for securing the specimen, another of the opposing arms having a further fixture for securing the specimen, the fixture and the further fixture being adjustable to increase or decrease the relative distance therebetween, and an assigned vibration location to which an exciter is engaged to apply excitation signals during testing the assigned vibration location including a hole having a screw thread for receiving an exciter.

* * * * *